US011221673B2

(12) United States Patent
Saisho et al.

(10) Patent No.: US 11,221,673 B2
(45) Date of Patent: Jan. 11, 2022

(54) ANALYSIS DEVICE, ANALYSIS METHOD, AND RECORDING MEDIUM

(71) Applicant: NIPPON TELEGRAPH AND TELEPHONE CORPORATION, Tokyo (JP)

(72) Inventors: Osamu Saisho, Musashino (JP); Shingo Tsukada, Musashino (JP); Kentaro Tanaka, Musashino (JP); Makoto Nakayama, Musashino (JP); Takashi Okada, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 0 days.

(21) Appl. No.: 17/057,695

(22) PCT Filed: May 14, 2019

(86) PCT No.: PCT/JP2019/019140
§ 371 (c)(1),
(2) Date: Nov. 23, 2020

(87) PCT Pub. No.: WO2019/230374
PCT Pub. Date: Dec. 5, 2019

(65) Prior Publication Data
US 2021/0200312 A1 Jul. 1, 2021

(30) Foreign Application Priority Data
Jun. 1, 2018 (JP) .............................. JP2018-106524

(51) Int. Cl.
*G06F 3/01* (2006.01)
*G06F 3/0484* (2013.01)

(52) U.S. Cl.
CPC .......... *G06F 3/015* (2013.01); *G06F 3/04847* (2013.01)

(58) Field of Classification Search
CPC ........................... G06F 3/015; G06F 3/044847
USPC ......................................................... 345/156
See application file for complete search history.

(56) References Cited

U.S. PATENT DOCUMENTS

| 2012/0232416 | A1* | 9/2012 | Gilham | ................ A61B 5/7246 600/515 |
| 2017/0311890 | A1* | 11/2017 | Esteller | .................. A61B 5/316 |
| 2018/0020990 | A1* | 1/2018 | Park | ........................ A61B 5/746 600/301 |
| 2018/0296102 | A1* | 10/2018 | Satish | ................... G06F 3/0488 |

OTHER PUBLICATIONS

Staude et al., "Onset detection in surface electromyographic signals: a systematic comparison of methods", EURASIP Journal on Applied Signal Processing, Jun. 1, 2001, 15 pages.

* cited by examiner

*Primary Examiner* — Calvin C Ma
(74) *Attorney, Agent, or Firm* — Xsensus LLP

(57) ABSTRACT

An analysis device according to the present invention includes a memory, and processing circuitry coupled to the memory and configured to analyze data indicating a biosignal by using a predetermined analysis technique and an updated parameter corresponding to the predetermined analysis technique every time the parameter is updated, control a display to display an analysis result obtained together with an interface capable of changing display modes in response to user's operation, and update the parameter based on change in the display modes for the interface.

7 Claims, 9 Drawing Sheets

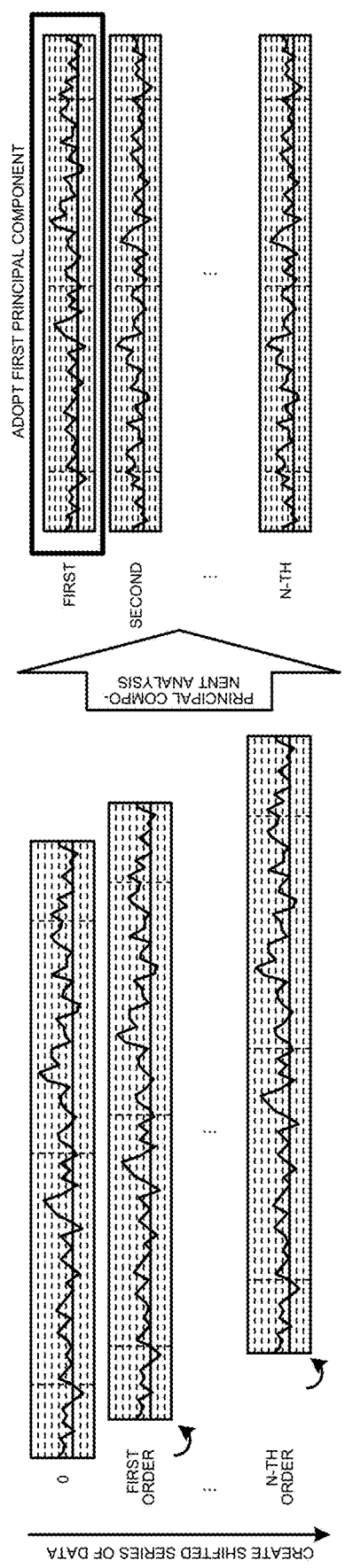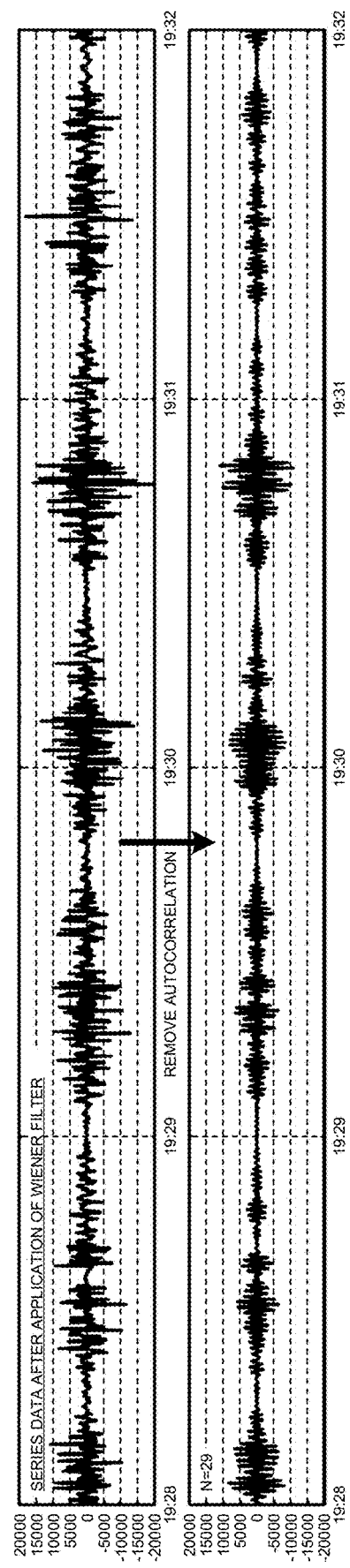
FIG.7

ANALYSIS DEVICE, ANALYSIS METHOD, AND RECORDING MEDIUM

CROSS-REFERENCE TO RELATED APPLICATIONS

The present application is based on PCT filing PCT/JP2019/019140, filed May 14, 2019, which claims priority to JP 2018-106524, filed Jun. 01, 2018, the entire contents of each are incorporated herein by reference.

TECHNICAL FIELD

The present invention relates to an analysis device, an analysis method, and a recording medium.

BACKGROUND ART

When a biosignal acquired from a sensor mounted on the human body is analyzed, noise or distortion occurring in the biosignal might influence analysis results in some cases. To handle this, there is a conventionally known method of removing, from analysis results, an influence of noise and distortion occurring in a biosignal.

For example, there are known methods of manually performing preprocessing by a person skilled in biosignal processing, including application of various filters such as a frequency filter to the biosignal, extraction of waveform patterns from the biosignal and conversion of the patterns to feature amounts. In addition, there is known a method of analyzing a biosignal by using a parameter and a processing flow of an analysis technique predetermined by a person skilled in biosignal processing.

CITATION LIST

Non Patent Literature

Non Patent Literature 1: Staude et al., "Onset detection in surface electromyographic signals: a systematic comparison of methods", EURASIP J ADV SIG PR, 2001.

SUMMARY OF THE INVENTION

Technical Problem

However, the conventional method has a problem of having difficulty in some cases in performing analysis of biosignals with ease and high efficiency. For example, the method of manually performing the preprocessing has problems of requiring high skill in biosignal processing, requiring much time for processing, and a risk of involving arbitrary operation. In addition, a method of determining the parameters and the processing flow in advance has a problem of having difficulty in some cases in managing an environmental change that occurs during biosignal measurement, for example.

Means for Solving the Problem

In order to solve the above problem and achieve a goal, an analysis device according to the present invention includes: a memory; and processing circuitry coupled to the memory and configured to: analyze data indicating a biosignal by using a predetermined analysis technique and an updated parameter corresponding to the predetermined analysis technique every time the parameter is updated, control a display to display an analysis result obtained together with an interface capable of changing display modes in response to user's operation, and update the parameter based on change in the display modes for the interface.

Effects of Invention

According to the present invention, biosignal analysis can be performed with ease and high efficiency.

BRIEF DESCRIPTION OF DRAWINGS

FIG. 7 is a diagram illustrating a whitening filter.

DESCRIPTION OF EMBODIMENTS

Hereinafter, embodiments of an analysis device, an analysis method, and an analysis program according to the present application will be described in detail with reference to the drawings. The present invention is not limited to the embodiments described below.

Outline of First Embodiment

Figure 1:
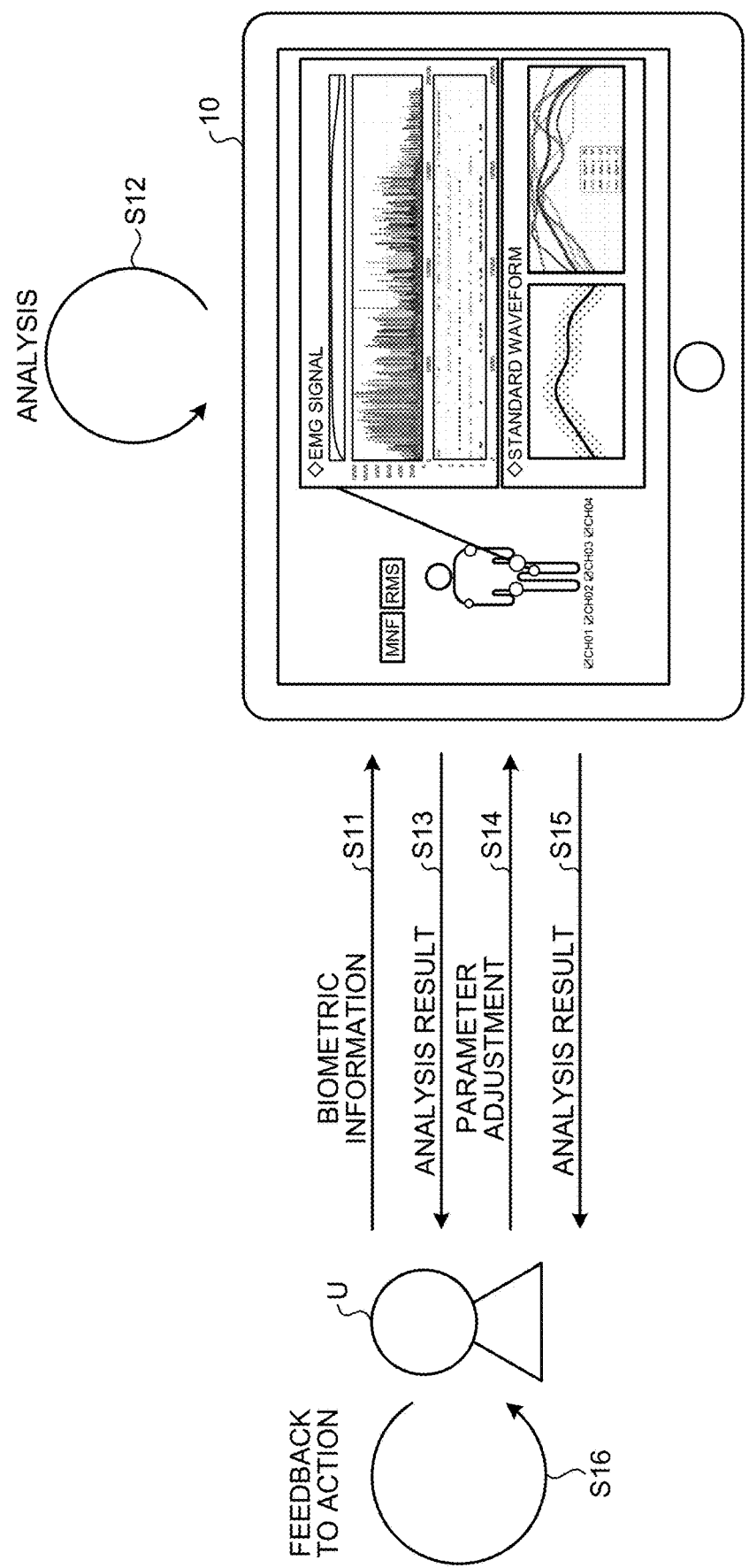
FIG. 1 is a diagram illustrating an outline of an analysis device according to a first embodiment.

First, an outline of an analysis device according to a first embodiment will be described with reference to FIG. 1. FIG. 1 is a diagram illustrating an outline of the analysis device according to the first embodiment. As illustrated in FIG. 1, a user U provides biometric information to an analysis device 10 (step S11). At this time, for example, the user U transmits data acquired by a sensor group worn on the user's body to the analysis device 10 by wireless communication using a data transmission device. Examples of the biometric information include myoelectric potential, body temperature, and heart rate. Furthermore, for example, the user U may provide biometric information using hitoe (registered trademark), (Reference URL: http://www.ntt.co.jp/ntt-tec/special/hitoe/index.html), which is a clothes-type wearable measuring instrument.

The analysis device 10 analyzes the biometric information provided from the user U (step S12). At this time, the analysis device 10 can execute analysis after performing preprocessing and feature amount extraction. Subsequently, the analysis device 10 displays analysis results on a screen together with a predetermined interface so as to be presented to the user U (step S13). For example, the analysis results displayed by the analysis device 10 may include not only the final analysis results but also a graph indicating the preprocessed biosignal.

Here, the user U refers to the analysis results displayed on the screen and adjusts the parameter by operating the interface (step S14). Subsequently, the analysis device 10 performs the analysis again using the adjusted parameters and presents the analysis results (step S15). Subsequently, the user U feeds back the analysis results to the action (step S16).

This enables, in the present embodiment, the user U to adjust the parameters used in the analysis simply by operating the interface displayed on the analysis result screen. Therefore, according to the present embodiment, the user U can change the display result to fit a personal taste by an intuitive operation and provide effective feedback.

Configuration of First Embodiment

Figure 2:
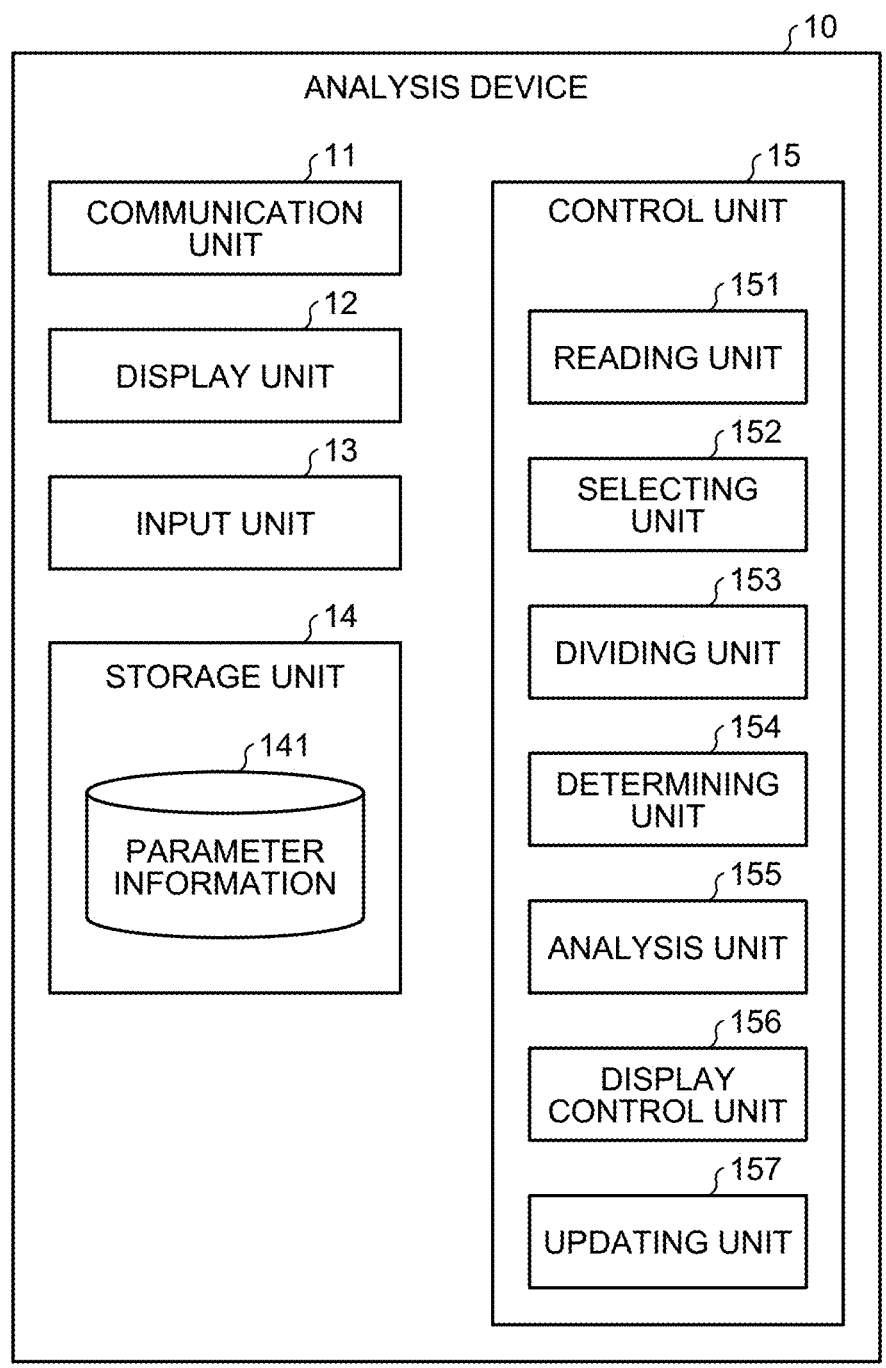
FIG. 2 is a diagram illustrating an example of a configuration of the analysis device according to the first embodiment.

A configuration of the analysis device according to the first embodiment will be described with reference to FIG. 2. FIG. 2 is a diagram illustrating an example of a configuration of the analysis device according to the first embodiment. As illustrated in FIG. 2, the analysis device 10 includes a communication unit 11, a display unit 12, an input unit 13, a storage unit 14, and a control unit 15.

The communication unit 11 performs data communication with other devices via a network. For example, the communication unit 11 includes a network interface card (NIC). For example, the communication unit 11 performs wireless communication between the sensor attached to the user U and the data transmission device.

The display unit 12 outputs data by displaying a screen or the like. For example, the display unit 12 is a display device such as a display. The input unit 13 receives data input from the user U. The input unit 13 is, for example, an input device such as a mouse or a keyboard. The display unit 12 and the input unit 13 may be touch panel displays.

The storage unit 14 is a storage device such as a hard disk drive (HDD), a solid state drive (SSD), and an optical disk. The storage unit 14 may be a data-rewritable semiconductor memory devices such as random access memory (RAM), a flash drive, or non volatile static random access memory (NVSRAM). The storage unit 14 stores an operating system (OS) and various programs executed by the analysis device 10. Furthermore, the storage unit 14 stores various types of information used in execution of the program. The storage unit 14 also stores parameter information 141.

The storage unit 14 stores parameters used for analysis of biometric information, as the parameter information 141. In a case where the parameter is represented by the prior distribution, the parameter information 141 includes the mean and variance of the prior distribution. Furthermore, in a case where a likelihood function is used to determine the parameter, the parameter information 141 includes the likelihood function.

The control unit 15 performs overall control of the analysis device 10. The control unit 15 is implemented by, for example, an electronic circuit such as a central processing unit (CPU) or a micro processing unit (MPU), or an integrated circuit such as an application specific integrated circuit (ASIC) and a field programmable gate array (FPGA). Furthermore, the control unit 15 includes internal memory for storing programs and control data that define various processing procedures, and executes individual processes using the internal memory.

Furthermore, various programs are operated to enable the control unit 15 to function as various processing units. For example, the control unit 15 includes a reading unit 151, a selecting unit 152, a dividing unit 153, a determining unit 154, an analysis unit 155, a display control unit 156, and an updating unit 157.

The reading unit 151 reads data indicating a biosignal. For example, the data read by the reading unit 151 is received by the communication unit 11. The data indicating a biosignal is acquired at each of times, and, for example, when the time is t, the data in a range from t=0 to t=T is represented by Formula (1).

$$x = (x_1, x_2, \ldots, x_t, \ldots, x_T) \qquad (1)$$

The selecting unit 152 receives selection of an analysis technique to be executed. The analysis device 10 can prepare a plurality of executable analysis techniques in advance and perform analysis using the analysis technique selected by the user U. For example, analysis techniques include onset detection, root mean square (RMS) calculation, mean frequency (MNF) calculation, or the like. Furthermore, whether each of analysis techniques has been selected is stored as in C of Formula (2). Each of elements of C in Formula (2) corresponds to each of the analysis techniques, indicating 1 for selection and 0 for non-selection.

$$C = \{1, 0, \ldots, 1\} \qquad (2)$$

Furthermore, a predetermined preprocessing flow corresponds to each of analysis techniques. The components of the preprocessing flow include various frequency filters, a Wiener filter, a whitening filter, smoothing, rectification or the like. In the following description, the analysis result is assumed to include results of preprocessing applied on the data indicating biosignals.

The dividing unit 153 clusters the data in the time-series direction for each biosignal strength, and then divides the data based on the change in the appearance frequency for each of clusters. Furthermore, the dividing unit 153 divides the data before and after the time point at which the magnitude of change in the appearance frequency of the clusters having strength of a predetermined value or less among the clusters is a predetermined value or above. For example, the data divided into n pieces by the dividing unit 153 is expressed as in Formula (3). The symbol X in Formula (3) represents a set of divided data $x_i$ (where i is 1 to n).

$$X = \{x_1, \ldots, x_i, \ldots, x_n\} (x_i \ldots x_i \ldots x_n) = x \qquad (3)$$

The data read by the reading unit 151 is biosignal data that is measured continuously. Therefore, the dividing unit 153 automatically detects a position to be divided by using an approximated generalized likelihood-ratio (AGLR) method (refer to Non Patent Literature 1, for example). Here, the location detected by the dividing unit 153 is a position where the parameters used for the preprocessing will be changed before and after the position.

Figure 3:
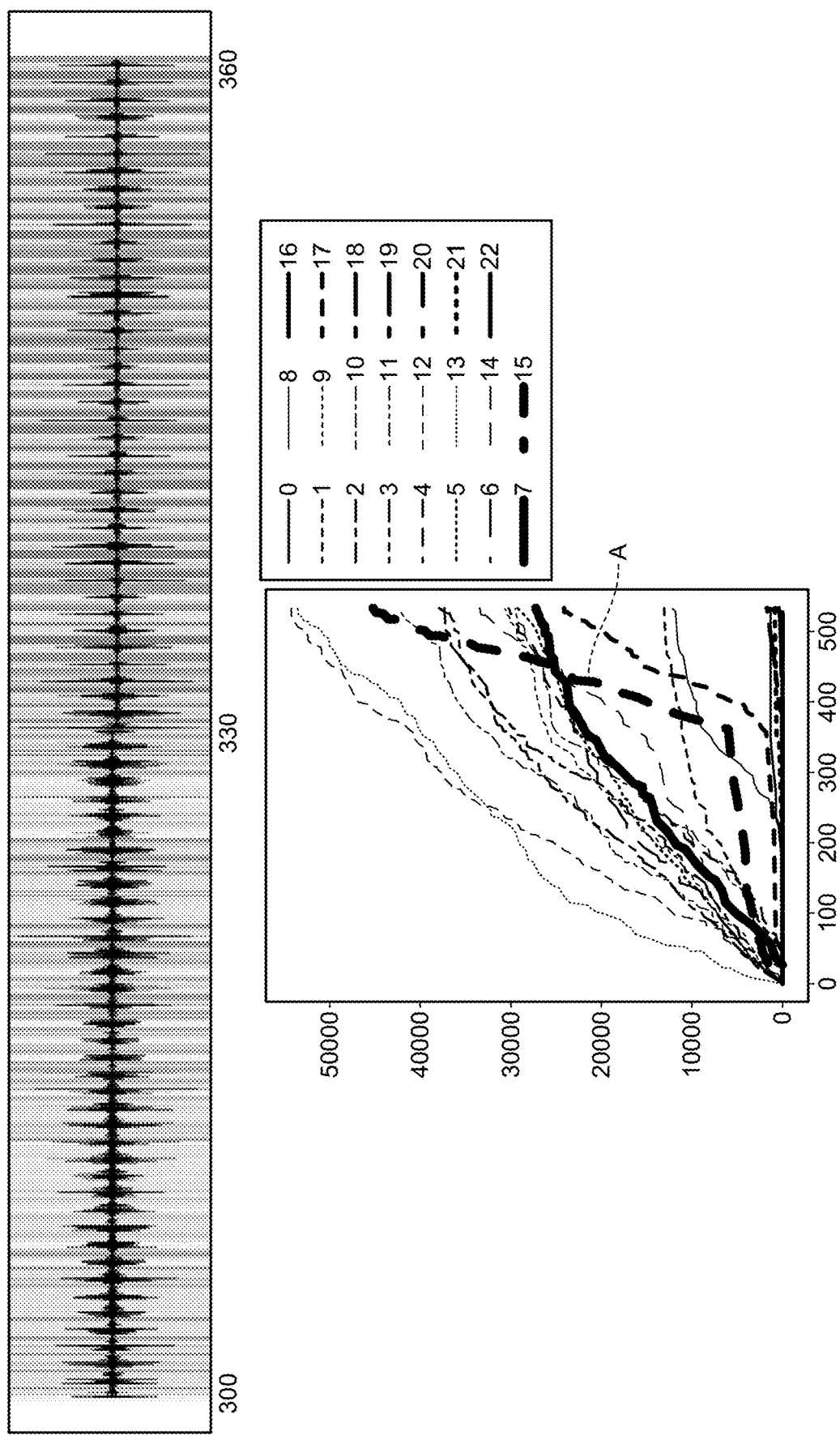
FIG. 3 is a diagram illustrating division of data.

The division of data performed by the dividing unit 153 will be described with reference to FIG. 3. FIG. 3 is a diagram illustrating division of data. First, the dividing unit 153 performs clustering in the time-series direction according to the strength of the biosignal. In the example of FIG. 3, the dividing unit 153 clusters the data into 23 clusters.

Subsequently, the dividing unit 153 divides the data before and after the time point where the appearance frequency of the predetermined cluster changes significantly. In the example of FIG. 3, the appearance frequency of the cluster indicated by A rapidly increases near the point where t=330. Therefore, the dividing unit 153 divides the data before and after the point where t=330.

Here, a change in the appearance frequency of a cluster having high biosignal strength indicates a change in the behavior of the user U in some cases. For example, when the user U is tired, there might be a change in the appearance frequency of a high strength signal.

In contrast, a change in the appearance frequency of a cluster having low biosignal strength indicates a change in the environment or a change in the state of the user U in some cases. For example, when an electric signal is acquired using an electrode attached to the skin of the user U, the influence of perspiration or the like appears as a change in the biosignal having low strength.

Therefore, when there is a change in the appearance frequency of the signal of the cluster having low strength, the dividing unit 153 can divide the data before and after the change. With this configuration, the analysis device 10 can set parameters for each of pieces of divided data in consideration of changes in the environment and the state of the user U. In the following description, the parameter mainly refers to the parameter used in preprocessing.

The determining unit 154 determines parameters so as to optimize the likelihood function regarding the prior distribution set for each of the parameters. Specifically, the determining unit 154 determines the parameter $\Theta_i$ of the divided data $x_i$ by maximizing the likelihood function as in Formula (4). That is, the determining unit 154 uses the C in Formula (2) indicating the selected analysis technique and determines the parameters to be used in the preprocessing, by using the product of the likelihood $P(x_i|\Theta,C)$ and the prior probability $P(\Theta|C)$ of the parameter. Furthermore, in the following description, the parameters determined by the determining unit 154 are referred to as initial parameters.

$$\Theta_i = \arg\max_{\Theta} P(x_i|\Theta, C)P(\Theta|C) \tag{4}$$

The analysis unit 155 analyzes data indicating a biosignal by using a predetermined analysis technique and an updated parameter corresponding to the predetermined analysis technique every time the parameter is updated. In addition, in a case where the data is divided, the analysis unit 155 performs analysis using the parameter set for each of pieces of data divided by the dividing unit 153. In addition, in a case where the determining unit 154 has determined the parameter, the analysis unit 155 performs the analysis using the parameter determined by the determining unit 154.

Figure 4:
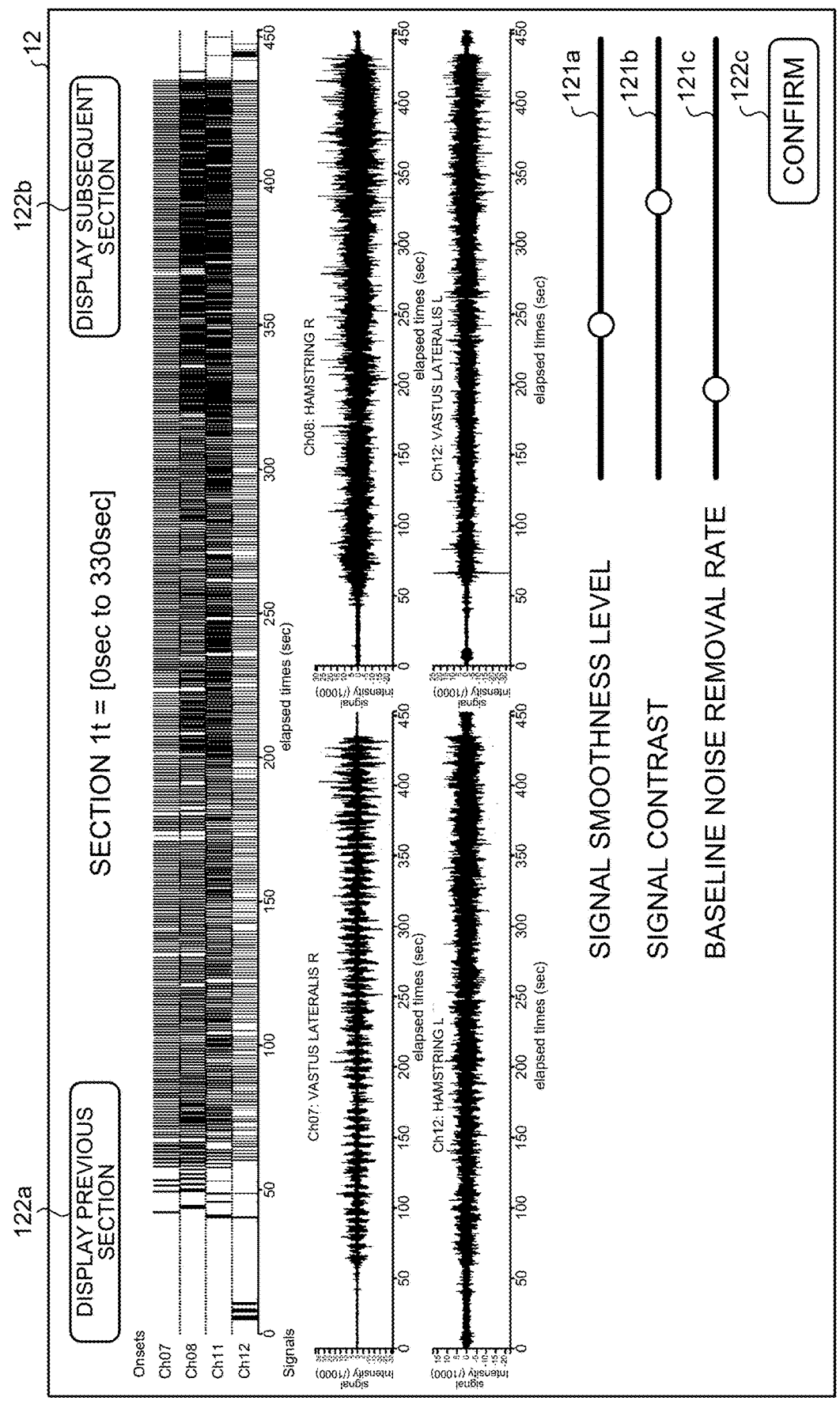
FIG. 4 is a diagram illustrating an example of an analysis result screen of the analysis device according to the first embodiment.

The display control unit 156 controls the display unit 12 to display the analysis result obtained by the analysis unit 155 together with the interface capable of changing the display mode in response to user's operation. FIG. 4 is a diagram illustrating an example of an analysis result screen of the analysis device according to the first embodiment. For example, as illustrated in FIG. 4, the display control unit 156 controls to display, as an interface, a seek bar associated with a word describing a predetermined parameter. The interface displayed by the display control unit 156 is not limited to the seek bar. The display control unit 156 may display a pull-down list or a scroll-wheel type list.

As illustrated in FIG. 4, the display control unit 156 controls the display unit 12 to display a graph indicating the result of onset detection and the data of individual biosignals subjected to the preprocessing. Furthermore, the display control unit 156 controls the display unit 12 to display a seek bar 121a, a seek bar 121b, a seek bar 121c, a button 122a, a button 122b, and a button 122c.

As illustrated in FIG. 4, the display control unit 156 controls to display the word "signal smoothness" indicating a predetermined parameter corresponding to the seek bar 121a. Furthermore, the display control unit 156 controls to display the word "signal contrast" indicating a predetermined parameter corresponding to the seek bar 121b. Furthermore, the display control unit 156 controls to display the word "baseline noise removal rate" indicating a predetermined parameter corresponding to the seek bar 121c.

The example of FIG. 4 displays an analysis result of the data within the section from t=0 to t=330 out of the data divided by the dividing unit 153. Here, when the button 122a and the button 122b are pressed, the display control unit 156 controls to display an analysis result of the divided data corresponding to the previous section and the subsequent section, individually. The process to be performed when each of seek bars is operated and the process to be performed when the button 122c is operated will be described below together with the description of the updating unit 157.

The updating unit 157 updates the parameter based on the change in the display mode for the interface. The position of the slider of each of the seek bars illustrated in FIG. 4 is an example of a display mode. That is, the updating unit 157 updates the parameter in a case where the position of the slider of each of seek bars has been changed. The range of parameter that can be changed by operating the seek bar may be limited to the range of 1σ in the prior distribution.

For example, an example of conceivable preprocessing is to perform a process of smoothing by calculating a moving average for each of predetermined sections on biosignal data. Here, the position of the slider of the seek bar 121a is assumed to be associated with the parameter indicating the length of the section. The updating unit 157 performs updating so that the parameter is increased when the position of the slider of the seek bar 121a moves to the right. Subsequently, the display control unit 156 displays a result of performing analysis again with the updated parameter.

Therefore, even when the user U does not recognize execution of calculation of the moving average, the user U can perform parameter adjustment to achieve a higher smoothing level in the preprocessed data just by moving the slider of the seek bar 121a to the right. Note that each of interfaces may be associated with one parameter or associated with a combination of a plurality of parameters.

Furthermore, in a case where an operation of confirming the operation of changing the display mode of the interface is performed, the updating unit 157 updates the prior distribution and the likelihood function based on the change in the display mode. The operation of pressing the button 122c of FIG. 4 is an example of operation of confirming the operation of changing the display mode. When the button 122c is pressed, the updating unit 157 updates the prior distribution and the likelihood function based on the position of the slider of each of seek bars at that point of time. For example, the updating unit 157 can perform updating so that the value corresponding to the position of the slider becomes an average in the prior distribution of the parameters.

Preprocessing

Figure 5:
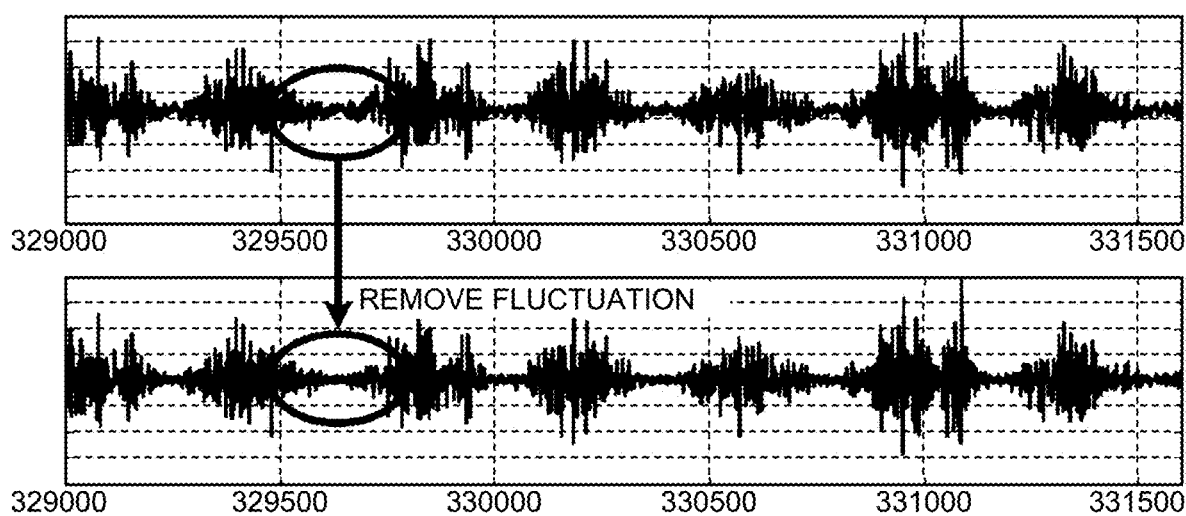
FIG. 5 is a diagram illustrating a frequency filter.
Figure 6:
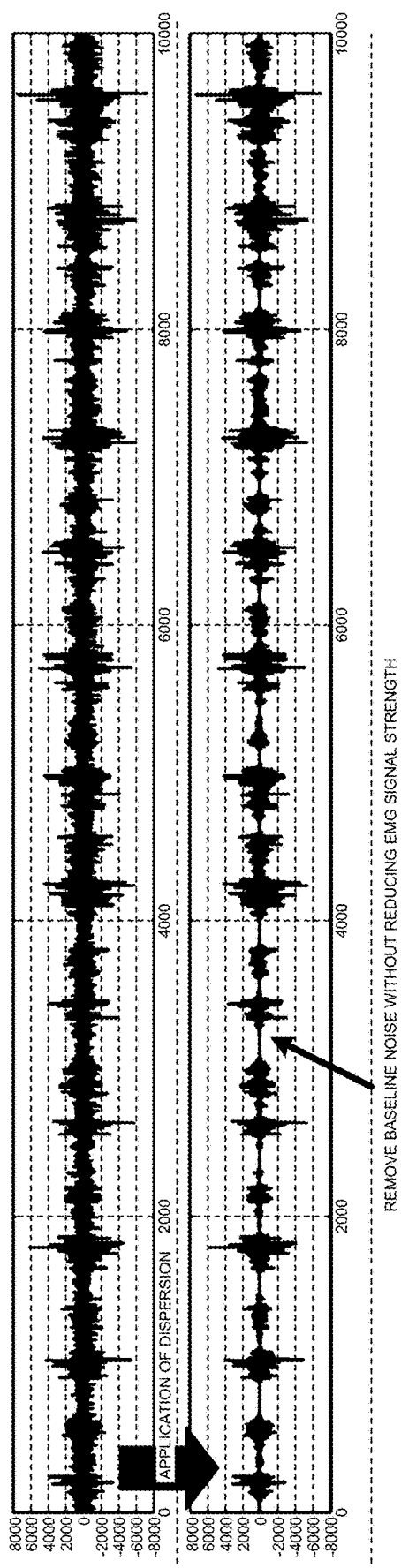
FIG. 6 is a diagram illustrating a Wiener filter.

An example of the preprocessing performed by the analysis unit 155 will be described with reference to FIGS. 5 to 7. FIG. 5 is a diagram illustrating a frequency filter. FIG. 6 is a diagram illustrating a Wiener filter. FIG. 7 is a diagram illustrating a whitening filter.

As illustrated in FIG. 5, the analysis unit 155 can remove a signal of a specific frequency and remove fluctuation by using a frequency filter. The display control unit 156 can also control the display unit 12 to display an interface capable of adjusting the upper limit value, the lower limit value, the range, or the like of the frequency to be removed by the frequency filter.

As illustrated in FIG. 6, the analysis unit 155 can remove the baseline noise using the Wiener filter without reducing the signal strength. Furthermore, as illustrated in FIG. 4, the display control unit 156 can control the display unit 12 to display the seek bar 121c capable of adjusting the removal rate of the baseline noise in the use of the Wiener filter.

As illustrated in FIG. 7, the analysis unit 155 can remove the autocorrelation of the signal by using a whitening filter. When the whitening filter is used, the analysis unit 155 creates N pieces of data that are shifted by a predetermined width in the time-series direction based on the original signal data and performs a principal component analysis on the N pieces of data to obtain a first principal component. In addition, the display control unit 156 can control the display unit 12 to display an interface capable of adjusting the number N of pieces of shifted data in the whitening filter.

Processes in First Embodiment

Figure 8:
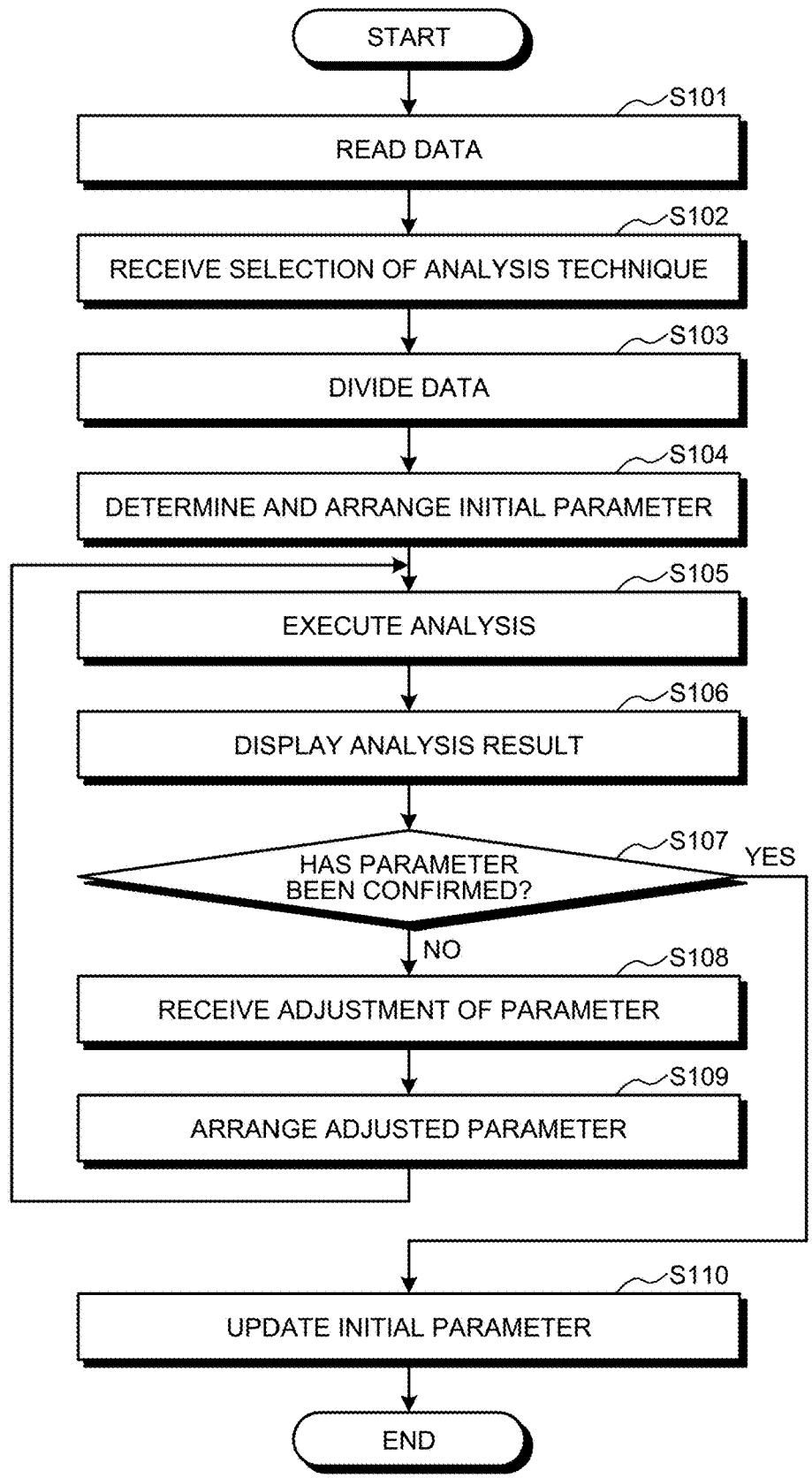
FIG. 8 is a flowchart illustrating a processing flow of the analysis device according to the first embodiment.

A processing flow of the analysis device 10 will be described with reference to FIG. 8. FIG. 8 is a flowchart illustrating a processing flow of the analysis device 10 according to the first embodiment. As illustrated in FIG. 8, the analysis device 10 reads data of the biosignal to be analyzed (step S101). Next, the analysis device 10 receives selection of the analysis technique (step S102).

Here, the analysis device 10 divides the data (step S103). Subsequently, the analysis device 10 determines and arranges initial parameters for each of the divided pieces of data (step S104).

Subsequently, the analysis device 10 executes analysis using the arranged parameters (step S105). At this time, the analysis device 10 performs preprocessing on the data and then performs analysis using the selected analysis technique. Thereafter, the analysis device 10 displays an analysis result together with a parameter adjustment interface (step S106).

Until confirmation of the parameter (step S107, No), the analysis device 10 accepts parameter adjustment via the interface (step S108), arranges the adjusted parameter (step S109), and proceeds to execution of analysis (step S105).

In contrast, after confirmation of the parameter (step S107, Yes), the analysis device 10 updates an initial parameter (step S110). Specifically, the analysis device 10 updates prior distribution of parameters and a likelihood function to be used at determination of the initial parameters in step S104.

Therefore, in a case where parameters are adjusted every time the flow of FIG. 8 is executed, the initial parameters determined in step S104 would be different even with the same read data or the same selected analysis technique.

Effects of First Embodiment

The analysis unit 155 analyzes data indicating a biosignal by using a predetermined analysis technique and an updated parameter corresponding to the predetermined analysis technique every time the parameter is updated. The display control unit 156 controls the display unit to display the analysis result obtained by the analysis unit 155 together with the interface capable of changing the display mode in response to user's operation. Furthermore, the updating unit 157 updates the parameter based on the change in the display mode for the interface. Therefore, according to the present embodiment, the user can intuitively adjust the parameters while checking the analysis result at appropriate times simply by operating the interface, leading to achievement of biosignal analysis with ease and high efficiency.

In addition, in this embodiment, the data analysis and the display of the analysis result can be automatically performed every time the biosignal data is acquired, making it possible to display the analysis result continuously and in real time to the user.

The dividing unit 153 clusters the data in the time-series direction for each biosignal strength, and then divides the data based on the change in the appearance frequency for each of clusters. In addition, the analysis unit 155 performs analysis using the parameter set for each of pieces of data divided by the dividing unit 153. This makes it possible to set parameters suitable for the data even when the properties of the data change in time series. In addition, in the present embodiment, due to automation of the division of data, which has been conventionally performed by a specialist afterwards, it is possible to perform the division in real time when the biosignal data is acquired.

The dividing unit 153 divides the data before and after the time point at which the magnitude of change in the appearance frequency of the cluster having strength of a predetermined value or less among the clusters is a predetermined value or above. This makes it possible to set and adjust the parameters in consideration of changes in the environment and the state of the user.

The display control unit 156 controls to display, as an interface, a seek bar associated with a word describing a predetermined parameter. This makes it possible to clearly present the user with the state how the analysis result changes by operating the interface.

The determining unit 154 determines parameters so as to optimize the likelihood function regarding the prior distribution set for each of the parameters. The analysis unit 155 also performs analysis using the parameters determined by the determining unit 154. Furthermore, in a case where an operation of confirming the operation of changing the display mode of the interface is performed, the updating unit 157 updates the prior distribution and the likelihood function based on the change in the display mode. This makes it possible to set appropriate parameters suited to the user's preference and analysis application.

System Configuration, and Others

Individual components of the illustrated devices are functionally conceptual and need not necessarily be physically configured as illustrated. That is, the specific form of the dispersion and integration of the functions of the individual devices is not limited to those illustrated in the drawings, and whole or a part of the apparatus may be functionally or physically configured in dispersion or integration in arbitrary units in accordance with various loads, usage conditions, or the like. All or any part of each of processing functions performed by each of devices can be realized by a CPU and a program analyzed and executed by the CPU or can be realized as hardware using wired logic.

Moreover, it is possible to perform manually all or a part of the processes described as processes performed automatically among all the processes described in the present embodiments. Alternatively, it is possible to perform automatically with a known method all or a part of the processes described as processes performed manually among all the processes described in the present embodiments. Besides this, information including the processing procedure, control procedure, specific nomenclature, various pieces of data, and parameters as illustrated above in the description or the drawings can be appropriately changed unless otherwise noted.

Programs

As an embodiment, the analysis device 10 can be implemented by installing, on a desired computer, an analysis program to execute the above analysis as package software or online software. For example, by controlling the information processing device to execute the above analysis program, the information processing device can be controlled to function as the analysis device 10. The information processing device here includes a desktop or laptop personal computer. In addition, the information processing device also includes a mobile communication terminal such as a smartphone, a mobile phone, a personal handy-phone system (PHS), and a slate or tablet terminal such as a personal digital assistant (PDA).

The analysis device 10 can also be implemented as an analysis server device that uses a terminal device used by a user as a client and provides the client with the above-described analysis-related services. For example, the analysis server device is implemented as a server device that provides an analysis service that takes biosignal data as input and supplies an analysis result as output. In this case, the analysis server device may be implemented as a Web server, or may be implemented as a cloud that provides the above-described analysis-related service by outsourcing.

Figure 9:
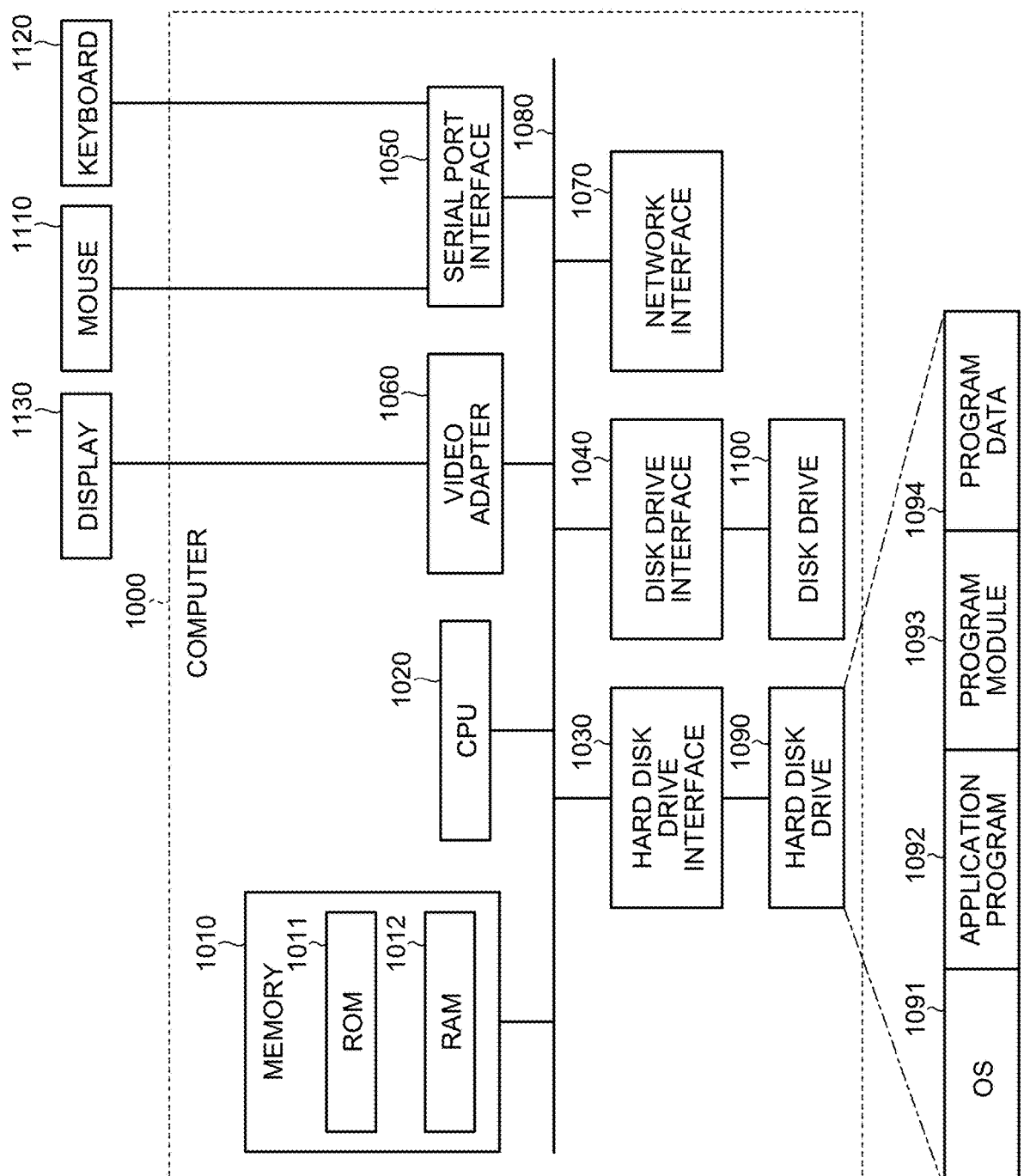
FIG. 9 is a diagram illustrating an example of a computer that executes an analysis program.

FIG. 9 is a diagram illustrating an example of a computer that executes an analysis program. A computer 1000 includes memory 1010 and a CPU 1020, for example. The computer 1000 also includes a hard disk drive interface 1030, a disk drive interface 1040, a serial port interface 1050, a video adapter 1060, and a network interface 1070. These components are connected by a bus 1080.

The memory 1010 includes read only memory (ROM) 1011 and RAM 1012. The ROM 1011 stores, for example, a boot program such as basic input output system (BIOS). The hard disk drive interface 1030 is connected to a hard disk drive 1090. The disk drive interface 1040 is connected to a disk drive 1100. For example, a detachable storage medium such as a magnetic disk or an optical disk is inserted into the disk drive 1100. The serial port interface 1050 is connected to a mouse 1110 and a keyboard 1120, for example. The video adapter 1060 is connected to a display 1130, for example.

The hard disk drive 1090 stores an OS 1091, an application program 1092, a program module 1093, and program data 1094, for example. That is, the program that defines each of processes of the analysis device 10 is implemented as a program module 1093 describing codes executable by a computer. The program module 1093 is stored in the hard disk drive 1090, for example. For example, the program module 1093 for executing processes similar to functional configurations of the analysis device 10 is stored in the hard disk drive 1090. The hard disk drive 1090 may be replaced with an SSD.

In addition, setting data used in the processes of the above-described embodiment is stored as program data 1094 in the memory 1010 and the hard disk drive 1090, for example. Subsequently, the CPU 1020 reads the program module 1093 and the program data 1094 stored in the memory 1010 or the hard disk drive 1090 onto the RAM 1012 as necessary to execute the processes of the above-described embodiment.

The program module 1093 and the program data 1094 is not necessarily to be stored in the hard disk drive 1090, but may be stored in a detachable storage medium and read out by the CPU 1020 via the disk drive 1100, for example. Alternatively, the program module 1093 and the program data 1094 may be stored in another computer connected via a network (local area network (LAN), wide area network (WAN), or the like). In addition, the program module 1093 and the program data 1094 may be read out from the other computer by the CPU 1020 via the network interface 1070.

REFERENCE SIGNS LIST

10 ANALYSIS DEVICE
11 COMMUNICATION UNIT
12 DISPLAY UNIT
13 INPUT UNIT
14 STORAGE UNIT
15 CONTROL UNIT
141 PARAMETER INFORMATION
151 READING UNIT
152 SELECTING UNIT
153 DIVIDING UNIT
154 DETERMINING UNIT
155 ANALYSIS UNIT
156 DISPLAY CONTROL UNIT
157 UPDATING UNIT

The invention claimed is:

1. An analysis device comprising:
a memory; and
processing circuitry coupled to the memory and configured to:
analyze data indicating a biosignal by using a predetermined analysis technique and an updated parameter corresponding to the predetermined analysis technique every time the parameter is updated,
control a display to display an analysis result obtained together with an interface capable of changing display modes in response to user's operation, and
update the parameter based on change in the display modes for the interface, wherein
the parameter is used to analyze biometric information, and in a case where the parameter is represented b a prior distribution, the parameter includes a mean and a variance of the prior distribution, wherein
the change in the display modes includes change in position of a slider of each of seek bars.

2. The analysis device according to claim 1, wherein the processing circuitry is further configured to:
cluster the data in a time-series direction for each strength of a biosignal and divide the data based on a change in an appearance frequency for each of clusters,
perform analysis by using a parameter set for each of pieces of data divided.

3. The analysis device according to claim 2, wherein the processing circuitry is further configured to divide the data before and after a time point at which a magnitude of the change in the appearance frequency of the cluster having strength of a predetermined value or less among the clusters is a predetermined value or above.

4. The analysis device according to claim 1, wherein the processing circuitry is further configured to control to display, as the interface, a seek bar associated with a word describing a predetermined parameter.

5. The analysis device according to claim 1, wherein the processing circuitry is further configured to:

determine a parameter so as to optimize a likelihood function regarding the prior distribution set for each of parameters, perform analysis by using the parameters determined, and update the prior distribution and the likelihood function based on a change in display modes of the interface in a case where an operation of confirming an operation of changing the display modes of the interface has been performed.

6. An analysis method comprising:

analyzing data indicating a biosignal by using a predetermined analysis technique and an updated parameter corresponding to the predetermined analysis technique every time the parameter is updated;

controlling a display to display an analysis result obtained together with an interface capable of changing display modes in response to user's operation, by processing circuitry; and updating the parameter based on the change in the display modes for the interface, wherein the parameter is used to analyze biometric information, and in a case where the parameter is represented by a prior distribution, the parameter includes a mean and a variance of the prior distribution, wherein the change in the display modes includes change in position of a slider of each of seek bars.

7. A non-transitory computer-readable recording medium storing therein an analysis program that causes a computer to execute a process comprising:

analyzing data indicating a biosignal by using a predetermined analysis technique and an updated parameter corresponding to the predetermined analysis technique every time the parameter is updated;

controlling a display to display an analysis result obtained together with an interface capable of changing display modes in response to user's operation; and updating the parameter based on the change in the display modes for the interface, wherein the parameter is used to analyze biometric information, and in a case where the parameter is represented by a prior distribution, the parameter includes a mean and a variance of the prior distribution wherein the change in the display modes includes change in position of a slider of each of seek bars.

* * * * *